United States Patent
Kawai et al.

(10) Patent No.: US 7,230,142 B1
(45) Date of Patent: Jun. 12, 2007

(54) PROCESS FOR PURIFYING FLUOROMETHYL 1,1,1,3,3,3-HEXAFLUOROISOPROPYL ETHER

(75) Inventors: Toshikazu Kawai, Saitama (JP); Matsue Kawamura, Saitama (JP)

(73) Assignee: Central Glass Company, Limited, Ube-shi (JP)

( * ) Notice: Subject to any disclaimer, the term of this patent is extended or adjusted under 35 U.S.C. 154(b) by 0 days.

(21) Appl. No.: 09/381,372

(22) PCT Filed: Mar. 3, 1999

(86) PCT No.: PCT/JP99/01006

§ 371 (c)(1),
(2), (4) Date: Sep. 20, 1999

(87) PCT Pub. No.: WO99/36959

PCT Pub. Date: Oct. 9, 1999

(30) Foreign Application Priority Data

Mar. 3, 1998 (JP) .................................. 10-051096

(51) Int. Cl.
*C07C 43/12* (2006.01)
*C07C 41/38* (2006.01)

(52) U.S. Cl. ...................................... 568/682; 568/683

(58) Field of Classification Search ................ 568/682, 568/683
See application file for complete search history.

(56) References Cited

U.S. PATENT DOCUMENTS 4,250,334 A    2/1981    Coon et al. .................. 568/683

FOREIGN PATENT DOCUMENTS

| EP | 703 450 A1 | 3/1996 |
| WO | WO 97/25303 | 7/1997 |

OTHER PUBLICATIONS

Abraham, M., Duce, P., and Prior, D. (1989) "Hydrogen Bonding, Part 9, Solute Proton Donor and Proton Acceptor Scales for Use in Drug Design". *J. Chem. Soc., Perkins Tranactions II* 1355-1375.

*Primary Examiner*—Rosalynd Keys
(74) *Attorney, Agent, or Firm*—Crowell & Moring LLP

(57) ABSTRACT

A process for purifying fluoromethyl 1,1,1,3,3,3-hexafluoroisopropyl ether containing at least 1,1,1,3,3,3-hexafluoroisopropyl alcohol. The purifying process comprises the treatment of causing fluoromethyl 1,1,1,3,3,3-hexafluoroisopropyl ether containing at least 1,1,1,3,3,3-hexafluoroisopropyl alcohol, to contact with a basic aqueous solution. The basic aqueous solution contains a basic substance in an amount providing a chemical equivalent ratio of the basic substance to 1,1,1,3,3,3-hexafluoroisopropyl alcohol being within a range of not less than 1.

9 Claims, No Drawings

PROCESS FOR PURIFYING FLUOROMETHYL 1,1,1,3,3,3-HEXAFLUOROISOPROPYL ETHER

FIELD OF THE INVENTION

This invention relates to a process for purifying fluoromethyl 1,1,1,3,3,3-hexafluoroisopropyl ether which is extensively utilized as a pharmaceutical, particularly as an inhalation anesthetic.

BACKGROUND TECHNIQUE

Hitherto fluoromethyl 1,1,1,3,3,3-hexafluoroisopropyl ether has been extensively utilized as an inhalation anesthetic which is safe for use. A method of producing fluoromethyl 1,1,1,3,3,3-hexafluoroisopropyl ether is described in detail in U.S. Pat. No. 4,250,334, and arranged as follows: First, concentric sulfuric acid and hydrogen fluoride are added to paraformaldehyde to obtain a reaction mixture. Then, 1,1,1,3,3,3-hexafluoroisopropyl alcohol is added dropwise to the reaction mixture upon being heated, thereby to generate gas which is to be collected. The collected gas contains unreacted 1,1,1,3,3,3-hexafluoroisopropyl alcohol, and by-products such as formal, acetal and the like, in addition to the objective product of fluoromethyl 1,1,1,3,3,3-hexafluoroisopropyl ether.

Besides, International Publication No. WO97/25303 describes a method of producing fluoromethyl 1,1,1,3,3,3-hexafluoroisopropyl ether, arranged such that bis(fluoromethyl)ether, 1,1,1,3,3,3-hexafluoroisopropyl alcohol and sulfuric acid are mixed with each other thereby to obtain fluoromethyl 1,1,1,3,3,3-hexafluoroisopropyl ether together with unreacted bis(fluoromethyl)ether and acetal.

Regarding the above production methods of fluoromethyl 1,1,1,3,3,3-hexafluoroisopropyl ether, 1,1,1,3,3,3-hexafluoroisopropyl alcohol has the generally same boiling point (about 58.6° C.) as that of the objective product (fluoromethyl 1,1,1,3,3,3-hexafluoroisopropyl ether), and therefore it seems that the recovered objective product contains 1,1,1,3,3,3-hexafluoroisopropyl alcohol though the content of 1,1,1,3,3,3-hexafluoroisopropyl alcohol is different in accordance with reaction conditions.

In regard to the above, it is impossible to separate 1,1,1,3,3,3-hexafluoroisopropyl alcohol from fluoromethyl 1,1,1,3,3,3-hexafluoroisopropyl ether under distillation which is the most commonly used for purification of organic substances, since they have the generally same boiling points. Additionally, separation of them is impossible even under a separation method employing the difference in freezing point (−68° C. and −3.3° C.) between them. Additionally, even though 1,1,1,3,3,3-hexafluoroisopropyl alcohol is soluble in water in any mixing ratios between them, it cannot be sufficiently removed upon rinsing with water.

DISCLOSURE OF THE INVENTION

In view of the above conventional problems, the present inventors have made investigation and study on processes to obtain fluoromethyl 1,1,1,3,3,3-hexafluoroisopropyl ether which substantially does not contain 1,1,1,3,3,3-hexafluoroisopropyl alcohol without affecting useful fluoromethyl 1,1,1,3,3,3-hexafluoroisopropyl ether. As a result, the present inventors have found that 1,1,1,3,3,3-hexafluoroisopropyl alcohol can effectively removed by causing fluoromethyl 1,1,1,3,3,3-hexafluoroisopropyl ether containing 1,1,1,3,3,3-hexafluoroisopropyl alcohol, to contact with a basic aqueous solution, and have reached the present invention.

It is an object of the present invention to provide an improved process for purifying fluoromethyl 1,1,1,3,3,3-hexafluoroisopropyl ether, which can effectively overcome drawbacks encountered in conventional processes for purifying fluoromethyl 1,1,1,3,3,3-hexafluoroisopropyl ether.

Another object of the present invention is to provide an improved process for purifying fluoromethyl 1,1,1,3,3,3-hexafluoroisopropyl ether, which can effectively highly purify fluoromethyl 1,1,1,3,3,3-hexafluoroisopropyl ether containing 1,1,1,3,3,3-hexafluoroisopropyl alcohol (difficult to be removed by other measures) to such an extent as to be required for a medicine, even though the process is simple in operation.

A further object of the present invention is to provide an improved process for purifying fluoromethyl 1,1,1,3,3,3-hexafluoroisopropyl ether, which can effectively lower the concentration of 1,1,1,3,3,3-hexafluoroisopropyl alcohol contained in fluoromethyl 1,1,1,3,3,3-hexafluoroisopropyl ether into such a level as to be permissible for a medicine. 1,1,1,3,3,3-hexafluoroisopropyl alcohol has not been able to be sufficiently removed by rinsing with water.

A first aspect of the present invention resides in a process for purifying fluoromethyl 1,1,1,3,3,3-hexafluoroisopropyl ether. The purifying process comprises the step of causing fluoromethyl 1,1,1,3,3,3-hexafluoroisopropyl ether containing at least 1,1,1,3,3,3-hexafluoroisopropyl alcohol, to contact with a basic aqueous solution which contains a basic substance in an amount providing a chemical equivalent of the basic substance to 1,1,1,3,3,3-hexafluoroisopropyl alcohol being within a range of not less than 1.

A second aspect of the present invention resides in a process for purifying fluoromethyl 1,1,1,3,3,3-hexafluoroisopropyl ether. The purifying process comprises (a) the step of providing fluoromethyl 1,1,1,3,3,3-hexafluoroisopropyl ether containing at least 1,1,1,3,3,3-hexafluoroisopropyl alcohol, and a basic aqueous solution which contains a basic substance in an amount providing a chemical equivalent ratio of the basic substance to 1,1,1,3,3,3-hexafluoroisopropyl alcohol being within a range of not less than 1; and (b) the step of causing the fluoromethyl 1,1,1,3,3,3-hexafluoroisopropyl ether containing 1,1,1,3,3,3-hexafluoroisopropyl alcohol, to contact with the basic aqueous solution containing the basic substance.

A third aspect of the present invention resides in a process for purifying fluoromethyl 1,1,1,3,3,3-hexafluoroisopropyl ether. The purifying process comprises (a) the step of providing fluoromethyl 1,1,1,3,3,3-hexafluoroisopropyl ether containing at least 1,1,1,3,3,3-hexafluoroisopropyl alcohol, and a basic aqueous solution which contains a basic substance in an amount providing a chemical equivalent ratio of the basic substance to 1,1,1,3,3,3-hexafluoroisopropyl alcohol being within a range of not less than 1; (b) the step of forming a reaction system in which inorganic acid radical is substantially absent; and (c) causing the fluoromethyl 1,1,1,3,3,3-hexafluoroisopropyl ether containing 1,1,1,3,3,3-hexafluoroisopropyl alcohol, to contact with the basic aqueous solution containing the basic substance.

A fourth aspect of the present invention resides in a process for purifying fluoromethyl 1,1,1,3,3,3-hexafluoroisopropyl ether. The purifying process comprises the step of causing fluoromethyl 1,1,1,3,3,3-hexafluoroisopropyl ether containing at least 1,1,1,3,3,3-hexafluoroisopropyl alcohol, to contact with basic aqueous solution containing a basic substance, in a reaction system in which inorganic acid radical is substantially absent.

A fifth aspect of the present invention resides in a process for purifying fluoromethyl 1,1,1,3,3,3-hexafluoroisopropyl ether. The purifying process comprises (a) the step of forming a reaction system in which inorganic acid radical is substantially absent; and (b) the step of causing fluoromethyl 1,1,1,3,3,3-hexafluoroisopropyl ether containing at least 1,1,1,3,3,3-hexafluoroisopropyl alcohol, to contact with a basic aqueous solution containing a basic substance, in the reaction system.

According to the purifying process of the present invention, fluoromethyl 1,1,1,3,3,3-hexafluoroisopropyl ether containing at least 1,1,1,3,3,3-hexafluoroisopropyl alcohol (which has not been able to be removed by other measures) can be effectively highly purified to such an extent as to be required for a medicine, even though the purifying process is simple in operation.

THE BEST MODE FOR CARRYING OUT THE INVENTION

According to the present invention, a process for purifying fluoromethyl 1,1,1,3,3,3-hexafluoroisopropyl ether, comprises the step (or treatment) of causing fluoromethyl 1,1,1,3,3,3-hexafluoroisopropyl ether containing at least 1,1,1,3,3,3-hexafluoroisopropyl alcohol, to contact with a basic aqueous solution which contains a basic substance in an amount providing a chemical equivalent ratio of the basic substance to 1,1,1,3,3,3-hexafluoroisopropyl alcohol being within a range of not less than 1. Here, the chemical equivalent ratio more specifically means a ratio represented by "the chemical equivalent of the basic substance/the chemical equivalent of 1,1,1,3,3,3-hexafluoroisopropyl alcohol". Additionally, the "chemical equivalent" means an acid-base equivalent on the assumption that the 1,1,1,3,3,3-hexafluoroisopropyl alcohol is a monobasic acid.

Under the above purifying process of the present invention, fluoromethyl 1,1,1,3,3,3-hexafluoroisopropyl ether which substantially does not contain 1,1,1,3,3,3-hexafluoroisopropyl alcohol can be obtained. The thus obtained fluoromethyl 1,1,1,3,3,3-hexafluoroisopropyl ether may be distilled after components which are difficult to be separated under distillation are removed, if necessary. Such distillation can separate components higher or lower in boiling point than fluoromethyl 1,1,1,3,3,3-hexafluoroisopropyl ether from fluoromethyl 1,1,1,3,3,3-hexafluoroisopropyl ether obtained according to the above purifying process, thereby providing highly pure fluoromethyl 1,1,1,3,3,3-hexafluoroisopropyl ether. However, such distillation may not be required in case that fluoromethyl 1,1,1,3,3,3-hexafluoroisopropyl ether obtained by the purifying process substantially does not contain impurities other than 1,1,1,3,3,3-hexafluoroisopropyl alcohol for the reason why fluoromethyl 1,1,1,3,3,3-hexafluoroisopropyl ether has been already distilled.

The basic aqueous solution used for removing 1,1,1,3,3,3-hexafluoroisopropyl alcohol in the above purifying process is an aqueous solution of a basic substance. The basic substance is a substance which exhibit basicity in the form of aqueous solution and therefore is not limited to a particular one. Examples of the basic substance are hydroxide, oxide and carbonate of alkali metal or alkaline-earth metal. The alkali metal includes lithium, sodium, potassium, rubidium, and cesium. The alkaline-earth metal includes magnesium, calcium, strontium, and barium. Preferable examples of the basic substance are sodium hydroxide, sodium oxide, sodium carbonate, potassium hydroxide, potassium oxide, potassium carbonate, lithium hydroxide, lithium oxide, lithium carbonate, rubidium hydroxide, rubidium oxide, rubidium carbonate, cesium hydroxide, magnesium hydroxide, calcium hydroxide, strontium hydroxide, and barium hydroxide. At least one of these compounds (examples) is used as the basic substance in the purifying process of the present invention. It is to be noted that sodium hydroxide and/or potassium hydroxide are more preferably used as the basic substance in the purifying process of the present invention.

The concentration of the basic aqueous solution is preferably adjusted in accordance with the content of 1,1,1,3,3,3-hexafluoroisopropyl alcohol in fluoromethyl 1,1,1,3,3,3-hexafluoroisopropyl ether. In case that the content of 1,1,1,3,3,3-hexafluoroisopropyl alcohol is not smaller than about 1% by weight ("high concentration"), the concentration of the basic aqueous solution is preferably within a range of from 0.01 to 20% by weight. Although the concentration of the basic substance in the solution is less than 0.01% by weight, the effect of the treatment is sufficient. However, the amount of the basic aqueous solution to be used becomes larger, which is not preferable from the viewpoint of a facility for accomplishing the purifying process of the present invention. If the concentration of the basic substance in the solution exceeds 20% by weight, the basic substance may slightly react with fluoromethyl 1,1,1,3,3,3-hexafluoroisopropyl ether, which is not preferable.

In case that the content of 1,1,1,3,3,3-hexafluoroisopropyl alcohol is less than about 1% by weight ("low concentration"), the concentration of the basic aqueous solution is preferably within a range of from 0.001 to 20% by weight, more preferably within a range of from 0.01 to 5% by weight, the most preferably within a range of from 0.01 to 3% by weight. Although the concentration of the basic substance in the solution is less than 0.01% by weight, the effect of the treatment is sufficient. However, the amount of the basic aqueous solution to be used becomes larger, which is not preferable from the viewpoint of the facility for accomplishing the purifying process of the present invention. If the concentration of the basic substance in the solution exceeds 20% by weight, the basic substance may slightly react with fluoromethyl 1,1,1,3,3,3-hexafluoroisopropyl ether, which is not preferable.

As discussed above, it is preferable that the content of the basic substance in the solution is adjusted in accordance with the content of 1,1,1,3,3,3-hexafluoroisopropyl alcohol in fluoromethyl 1,1,1,3,3,3-hexafluoroisopropyl ether, in which not less than one (chemical) equivalent of the base substance is preferably used to one (chemical) equivalent of fluoromethyl 1,1,1,3,3,3-hexafluoroisopropyl alcohol. More preferably 1 to 10 equivalents, the most preferably 1 to 3 equivalents of the base substance is used to one equivalent of 1,1,1,3,3,3-hexafluoroisopropyl alcohol. In case that the content of 1,1,1,3,3,3-hexafluoroisopropyl alcohol in fluoromethyl 1,1,1,3,3,3-hexafluoroisopropyl ether is relatively small ("low concentration"), it is preferable that the equivalent ratio of the basic substance to 1,1,1,3,3,3-hexafluoroisopropyl alcohol is within a range of from about 1 to about 2, from the viewpoint of lowering the content of 1,1,1,3,3,3-hexafluoroisopropyl alcohol and from the viewpoint of simplifying a process following the purifying process of the present invention. In case that acid is present in fluoromethyl 1,1,1,3,3,3-hexafluoroisopropyl ether in the above purifying process, it is preferable to increase the amount of the basic substance by an amount required for neutralization of the acid.

The purifying process of the present invention is carried out preferably at a temperature ranging from 0 to about 60° C. However, usually it is not necessary to heat or cool a reaction system for carrying out the purifying process, so that it is sufficient that the purifying process is carried out at room temperature. If the temperature exceeds 60° C., fluoromethyl 1,1,1,3,3,3-hexafluoroisopropyl ether may slightly decompose, which is not preferable. Besides, the purifying process is carried out at any pressures since the pressures cannot affect the result of the treatment under the purifying process. In this connection, the purifying process is carried out usually at a pressure ranging from 1 to 10 kg/cm$^2$.

In view of the fact that the present invention is intended to obtain fluoromethyl 1,1,1,3,3,3-hexafluoroisopropyl ether which substantially does not contain 1,1,1,3,3,3-hexafluoroisopropyl alcohol (more specifically, the content of 1,1,1,3,3,3-hexafluoroisopropyl alcohol is not larger than 1 ppm), it is preferable to cause the fluoromethyl 1,1,1,3,3,3-hexafluoroisopropyl ether to be previously subjected to a previous treatment in which fluoromethyl 1,1,1,3,3,3-hexafluoroisopropyl ether containing 1,1,1,3,3,3-hexafluoroisopropyl alcohol is contacted with the basic aqueous solution containing the basic substance in an amount providing the equivalent ratio of the basic substance to 1,1,1,3,3,3-hexafluoroisopropyl alcohol is not less than 1 so as to adjust the concentration of 1,1,1,3,3,3-hexafluoroisopropyl alcohol to a low level, in case that the content of 1,1,1,3,3,3-hexafluoroisopropyl alcohol in fluoromethyl 1,1,1,3,3,3-hexafluoroisopropyl ether is relatively high. Thereafter, fluoromethyl 1,1,1,3,3,3-hexafluoroisopropyl ether containing the thus adjusted 1,1,1,3,3,3-hexafluoroisopropyl alcohol is subjected to the purifying process in which fluoromethyl 1,1,1,3,3,3-hexafluoroisopropyl ether is contacted with the basic aqueous solution (low in concentration) containing the basic substance in an amount providing the equivalent ratio of the basic substance to 1,1,1,3,3,3-hexafluoroisopropyl alcohol being not less than 1.

As appreciated from the above, the purifying process of the present invention comprises the step or treatment of causing fluoromethyl 1,1,1,3,3,3-hexafluoroisopropyl ether containing at least 1,1,1,3,3,3-hexafluoroisopropyl alcohol, to be contacted with the basic aqueous solution. It is preferable that this process is accomplished in the reaction system in which substantially no inorganic acid radical is present. The inorganic acid radial includes ones of sulfuric acid, hydrofluoric acid and the like which may be added or used in reaction for producing fluoromethyl 1,1,1,3,3,3-hexafluoroisopropyl ether and in a post-treatment. The inorganic acid radial may includes other inorganic acid radials than the above. Thus, it is preferable that the purifying process of the present invention is applied to fluoromethyl 1,1,1,3,3,3-hexafluoroisopropyl ether (containing at least 1,1,1,3,3,3-hexafluoroisopropyl alcohol) from which at least acid substances have been previously removed. It will be understood that the passage "substantially no inorganic acid radial is present" herein means that the acid radicals (which have been able to be mixed into the reaction system during the reaction for producing fluoromethyl 1,1,1,3,3,3-hexafluoroisopropyl ether, and during the post-treatment) are hardly present in the reaction system as a result of rinsing with water and the basic aqueous solution, and therefore does not require a condition in which the inorganic acid radical is completely absent in the reaction system.

It will be understood that the treatment of the purifying process of the present invention is carried out under gas-liquid contact or liquid—liquid contact, and therefore a variety of measures or means for raising the efficiency of the treatment may be suitably selected and employed. Examples of such measures or means are stirring the content of the reaction system, using a sparger for stirring the content of the reaction system and the like, using a line mixer for mixing the content of the reaction system, using a pump for recirculating the content of the reaction system.

The examples described below are presented for illustrative purposes only, and are not intended to limit the scope of the invention of this application, which is as defined in the claims below.

EXAMPLE 1

Into a 300 ml flask provided with a reflux condenser and a stirrer, 100 g of fluoromethyl 1,1,1,3,3,3-hexafluoroisopropyl ether containing 10% by weight of 1,1,1,3,3,3-hexafluoroisopropyl alcohol was added to form a mixture. 95 g of a 5 wt % aqueous solution of sodium hydroxide was added to the mixture. Then, the mixture was stirred for 20 minutes while being kept at 35° C. At this time, the equivalent ratio of sodium hydroxide to 1,1,1,3,3,3-hexafluoroisopropyl alcohol was 2 in the mixture. Thereafter, stirring was stopped in which two layers were formed in the mixture in the flask. A part of the lower layer was sampled and subjected to a gas chromatographic analysis to analyze the organic matter in the lower layer. As a result of the analysis, it was confirmed that the lower layer contained 0.1% by weight of 1,1,1,3,3,3-hexafluoroisopropyl alcohol. At this time, no new substance was found in a gas chromatogram obtained by the analysis.

EXAMPLE 2

Into a 300 ml flask provided with a reflux condenser and a stirrer, 100 g of fluoromethyl 1,1,1,3,3,3-hexafluoroisopropyl ether containing 10% by weight of 1,1,1,3,3,3-hexafluoroisopropyl alcohol was added to form a mixture. 126 g of a 5 wt % aqueous solution of sodium carbonate ($Na_2CO_3$) was added to the mixture. Then, the mixture was stirred for 20 minutes while being kept at 35° C. At this time, the equivalent ratio of sodium carbonate to 1,1,1,3,3,3-hexafluoroisopropyl alcohol was 2 in the mixture. Thereafter, stirring was stopped in which two layers were formed in the mixture in the flask. A part of the lower layer was sampled and subjected to a gas chromatographic analysis to analyze the organic matter in the lower layer. As a result of the analysis, it was confirmed that the lower layer contained 0.8% by weight of 1,1,1,3,3,3-hexafluoroisopropyl alcohol. At this time, no new substance was found in a gas chromatogram obtained by the analysis.

EXAMPLE 3

Into a 300 ml flask provided with a reflux condenser and a stirrer, 100 g of fluoromethyl 1,1,1,3,3,3-hexafluoroisopropyl ether containing 0.25% by weight of 1,1,1,3,3,3-hexafluoroisopropyl alcohol was added to form a mixture. 71 g of a 0.1 wt % aqueous solution of sodium hydroxide was added to the mixture. Then, the mixture was stirred for 3 hours while being kept at 35° C. At this time, the equivalent ratio of sodium hydroxide to 1,1,1,3,3,3-hexafluoroisopropyl alcohol was 1.2 in the mixture. Thereafter, stirring was stopped in which two layers were formed in the mixture in the flask. A part of the lower layer was sampled and subjected to a gas chromatographic analysis to analyze the organic matter in the lower layer. As a result of the analysis, it was confirmed that the lower layer contained 1,1,1,3,3,3-hexafluoroisopropyl alcohol in an amount smaller than a detection limit (1 ppm). At this time, no new substance was found in a gas chromatogram obtained by the analysis.

COMPARATIVE EXAMPLE 1

Into a 300 ml flask provided with a reflux condenser and a stirrer, 100 g of fluoromethyl 1,1,1,3,3,3-hexafluoroisopropyl ether containing 10% by weight of 1,1,1,3,3,3-hexafluoroisopropyl alcohol was added to form a mixture. 95 g of pure water was added to the mixture. Then, the mixture was stirred for 20 minutes while being kept at 35° C. Thereafter, stirring was stopped in which two layers were formed in mixture in the flask. A part of the lower layer was sampled and subjected to a gas chromatographic analysis to analyze the organic matter in the lower layer. As a result of the analysis, it was confirmed that the lower layer contained 3.4% by weight of 1,1,1,3,3,3-hexafluoroisopropyl alcohol. At this time, no new substance was found in a gas chromatogram obtained by the analysis.

COMPARATIVE EXAMPLE 2

Into a 300 ml flask provided with a reflux condenser and a stirrer, 100 g of fluoromethyl 1,1,1,3,3,3-hexafluoroisopropyl ether containing 0.25% by weight of 1,1,1,3,3,3-hexafluoroisopropyl alcohol was added to form a mixture. 71 g of pure water was added to the mixture. Then, the mixture was stirred for 3 hours while being kept at 35° C. Thereafter, stirring was stopped in which two layers were formed in mixture in the flask. A part of the lower layer was sampled and subjected to a gas chromatographic analysis to analyze the organic matter in the lower layer. As a result of the analysis, it was confirmed that the lower layer contained 1,1,1,3,3,3-hexafluoroisopropyl alcohol in an amount of 0.25% by weight which was the same as the amount at a time prior to the above treatment. At this time, no new substance was found in a gas chromatogram obtained by the analysis.

COMPARATIVE EXAMPLE 3

Into a 300 ml autoclave provided with a stirrer, 100 g of fluoromethyl 1,1,1,3,3,3-hexafluoroisopropyl ether containing 5% by weight of 1,1,1,3,3,3-hexafluoroisopropyl alcohol was added to form a mixture. 119 g of a 5 wt % aqueous solution of sodium hydroxide was added to the mixture. Then, the mixture was stirred for 20 minutes while being kept at 70° C. At this time, the equivalent ratio of sodium hydroxide to 1,1,1,3,3,3-hexafluoroisopropyl alcohol was 5 in the mixture. Thereafter, stirring was stopped in which two layers were formed in the mixture in the flask. A part of the lower layer was sampled and subjected to a gas chromatographic analysis to analyze the organic matter in the lower layer. As a result of the analysis, it was confirmed that the lower layer contained 0.05% by weight of 1,1,1,3,3,3-hexafluoroisopropyl alcohol. At this time, the peak of a new substance corresponding to 0.12% by weight was found in a gas chromatogram obtained by the analysis.

As appreciated from the above, according to the purifying process of the present invention, the concentration of 1,1,1,3,3,3-hexafluoroisopropyl alcohol contained in fluoromethyl 1,1,1,3,3,3-hexafluoroisopropyl ether can be sharply lowered as compared with other conventional purifying methods. As a result, the process can effectively purify fluoromethyl 1,1,1,3,3,3-hexafluoroisopropyl ether containing 1,1,1,3,3,3-hexafluoroisopropyl alcohol to such an extent as to be required for a medicine under a circumstance where it has been difficult to remove 1,1,1,3,3,3-hexafluoroisopropyl alcohol, even though the purifying process of the present invention is simple in operation.

INDUSTRIAL APPLICABILITY

As discussed above, the process for purifying fluoromethyl 1,1,1,3,3,3-hexafluoroisopropyl ether, according to the present invention is used for purifying fluoromethyl 1,1,1,3,3,3-hexafluoroisopropyl ether containing at least 1,1,1,3,3,3-hexafluoroisopropyl alcohol, to an extent as to be required for a medicine.

The invention claimed is:

1. A process for purifying fluoromethyl 1,1,1,3,3,3-hexafluoroisopropyl ether, comprising:
   causing fluoromethyl 1,1,1,3,3,3-hexafluoroisopropyl ether containing at least 1,1,1,3,3,3-hexafluoroisopropyl alcohol in an amount not greater than about 0.25% by weight to contact with a basic aqueous solution which contains a basic substance in an amount providing a chemical equivalent ratio of said basic substance to 1,1,1,3,3,3-hexafluoroisopropyl alcohol being within a range of not less than 1 so as to remove the 1,1,1,3,3,3-hexafluoroisopropyl alcohol from the fluoromethyl 1,1,1,3,3,3-hexafluoroisopropyl ether.

2. A process as claimed in claim 1, wherein said chemical equivalent ratio is within a range of from 1 to 3.

3. A process as claimed in claim 1, wherein the causing is carried out at a temperature ranging from 0 to 60° C.

4. A process as claimed in claim 1, wherein said basic substance is at least one selected from the group consisting of hydroxide, oxide and carbonate of metal.

5. A process as claimed in claim 4, wherein said metal is at least one selected from the group consisting of alkali metal and alkaline-earth metal.

6. A process as claimed in claim 5, wherein said basic substance is at least one selected from the group consisting of sodium hydroxide, sodium oxide, sodium carbonate, potassium hydroxide, potassium oxide, potassium carbonate, lithium hydroxide, lithium oxide, lithium carbonate, rubidium hydroxide, rubidium oxide, rubidium carbonate, cesium hydroxide, magnesium hydroxide, calcium hydroxide, strontium hydroxide, and barium hydroxide.

7. A process as claimed in claim 1, wherein said basic aqueous solution of said basic substance has a concentration ranging from 0.001 to 20% by weight.

8. A process for purifying fluoromethyl 1,1,1,3,3,3-hexafluoroisopropyl ether, comprising:
   providing fluoromethyl 1,1,1,3,3,3-hexafluoroisopropyl ether containing at least 1,1,1,3,3,3-hexafluoroisopropyl alcohol in an amount not greater than about 0.25% by weight and a basic aqueous solution which contains a basic substance in an amount providing a chemical equivalent ratio of said basic substance to 1,1,1,3,3,3-hexafluoroisopropyl alcohol being within a range of not less than 1; and
   causing said fluoromethyl 1,1,1,3,3,3-hexafluoroisopropyl ether containing 1,1,1,3,3,3-hexafluoroisopropyl alcohol, to contact with said basic aqueous solution containing said basic substance so as to remove the 1,1,1,3,3,3-hexafluoroisopropyl alcohol from the fluoromethyl 1,1,1,3,3,3-hexafluoroisopropyl ether.

9. A process for purifying fluoromethyl 1,1,1,3,3,3-hexafluoroisopropyl ether, comprising:
   providing fluoromethyl 1,1,1,3,3,3-hexafluoroisopropyl ether containing at least 1,1,1,3,3,3-hexafluoroisopropyl alcohol in an amount not greater than about 0.25% by weight and a basic aqueous solution which contains a basic substance in an amount providing a chemical equivalent ratio of the basic substance to 1,1,1,3,3,3-hexafluoroisopropyl alcohol being within a range of not less than 1;
   forming a reaction system in which inorganic acid radical is substantially absent; and
   causing said fluoromethyl 1,1,1,3,3,3-hexafluoroisopropyl ether containing 1,1,1,3,3,3-hexafluoroisopropyl alcohol, to contact with said basic aqueous solution containing said basic substance so as to remove the 1,1,1,3,3,3-hexafluoroisopropyl alcohol from the fluoromethyl 1,1,1,3,3,3-hexafluoroisopropyl ether.

* * * * *